United States Patent [19]

Shimamura et al.

[11] Patent Number: 5,104,901
[45] Date of Patent: Apr. 14, 1992

[54] METHOD OF PREVENTING MYCOPLASMA INFECTION

[75] Inventors: Tadakatsu Shimamura, 4-4, Nishihara 1-chome, Shibuya-ku, Tokyo; Yukihiko Hara, Fujieda, both of Japan

[73] Assignees: Mitsui Norin Co., Ltd.; Tadakatsu Shimamura, both of Tokyo, Japan

[21] Appl. No.: 508,083

[22] Filed: Apr. 11, 1990

[30] Foreign Application Priority Data

Sep. 20, 1989 [JP] Japan ................................. 1-244716

[51] Int. Cl.$^5$ ............................................. A61K 35/78
[52] U.S. Cl. ................................. 514/783; 424/195.1; 549/399
[58] Field of Search ..................... 424/195.1; 549/399; 514/783

[56] References Cited

U.S. PATENT DOCUMENTS 3,812,266  5/1974  Sanderson ............................. 426/52
4,004,038  1/1977  Wickremasinghe ................. 426/422
4,913,909  4/1990  Hara et al. ........................... 424/688

OTHER PUBLICATIONS

Franzblau, Scott, Comparative In Vitro Antimicrobial Activity of Chinese Medicinal Herbs, J of Ethnopharmacology 15 (1986) 279-288.

Jawetz, Ernest Review of Medical Microbiology Appleton & Lange 1987.

*Primary Examiner*—Ronald W. Griffin
*Assistant Examiner*—Ralph G. Tomer
*Attorney, Agent, or Firm*—Frishauf, Holtz, Goodman & Woodward

[57] ABSTRACT

The effective ingredient in the inventive medicament against infection with mycoplasma is tea, e.g., black tea, or a tea polyphenol as a constituent of tea including epigallocatechin gallate, epicatechin gallate, epigallocatechin, epicatechin, (+) catechin and the isomer thereof, free theaflavin, theaflavin monogallates A and B and theaflavin digallate.

15 Claims, No Drawings

METHOD OF PREVENTING MYCOPLASMA INFECTION

BACKGROUND OF THE INVENTION

1. Field of the Invention

The present invention relates to a novel preventive medicament against infection with mycoplasma or, more particularly, to a preventive medicament against infection with mycoplasma having a mycoplasma-killing activity so as to exhibit an effect for inhibiting infection with mycoplasma.

2. Background Information

Mycoplasma is a unique microorganism which, different from bacteria, is devoid of cell walls to exhibit polymorphism and requires sterols and the like. In the microbiological classification it is intermediately positioned between bacteria and viruses. Some of mycoplasmas are known to act as a pathogenic microorganism against human beings including the pneumonic mycoplasma to cause pneumonia, ureaplasma to cause non-gonorrheal urethritis and the like. It is also reported that, in addition to these infectious diseases in the respiratory organs and urinogenital organs, mycoplasmas may have some relevancy to the etiological factors to cause various diseases concomitantly occurring as a complication of the above mentioned diseases such as lesions in the central nerval system typically exemplified by lesions in the cerebral nerves, chronic articular rheumatism, acute salpingitis, acute pelvic diseases and the like.

Despite the enormous volume of the investigational reports and the very long history of studies on mycoplasmas, no conclusive results have yet been established of the pathogenicity of mycoplasmas so that known chemotherapeutic medicaments are very limited including only macrolide antibiotics and tetracycline for the time being. Accordingly, it is eagerly desired to develop a novel anti-mycoplasma medicament which can be administered to patients without undesirable side effects to the human body.

SUMMARY OF THE INVENTION

An object of the present invention is to provide a novel medicament against infection with mycoplasma as mentioned above. The inventors have carried out extensive investigations of natural products to discover a substance capable of exhibiting the desired effect without the problems usually encountered by using chemically synthesized compounds.

Thus, the medicament of the present invention against infection with mycoplasma comprises tea as the medicinally effective ingredient.

Further, the medicament of the invention comprises polyphenol compounds in tea as the effective ingredient. The polyphenol compound in tea as the effective ingredient in the inventive medicament is selected from the group consisting of epigallocatechin gallate, epicatechin gallate, epigallocatechin, epicatechin, (+)catechin and the isomer thereof, free theaflavin, theaflavin monogallate A, theaflavin monogallate B and theaflavin digallate.

DETAILED DESCRIPTION OF THE PREFERRED EMBODIMENTS

The present invention provides a novel preventive medicament against infection with mycoplasma, of which tea is the effective ingredient.

The tea polyphenol compounds as the principal effective ingredients in the inventive medicament against infection with mycoplasma include the tea catechin compounds represented by the general formula (I) given below and the theaflavin compounds represented by the general formula (II) given below:

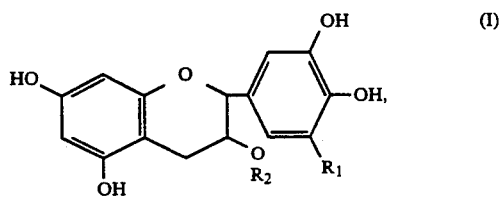

in which $R_1$ is a hydrogen atom or a hydroxy group and $R_2$ is a hydrogen atom or a 3,4,5-trihydroxy benzoyl group; and

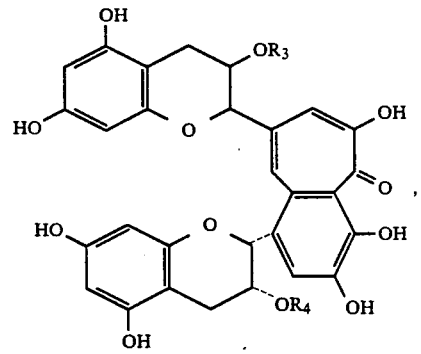

in which $R_3$ and $R_4$ are, each independently from the other, a hydrogen atom or a 3,4,5-trihydroxy benzoyl group.

Particular examples of the tea catechin compounds represented by the general formula (I) include: (−)epicatechin, which is a compound of the formula (I) with $R_1=H$ and $R_2=H$; (−)epigallocatechin, which is a compound of the formula (I) with $R_1=OH$ and $R_2=H$; (−)epicatechin gallate, which is a compound of the formula (I) with $R_1=H$ and $R_2=$3,4,5-trihydroxy benzoyl group; and (−)epigallocatechin gallate, which is a compound of the formula (I) with $R_1=OH$ and $R_2=$3,4,5-trihydroxy benzoyl group. Particular examples of the theaflavin compounds include: free theaflavin, which is a compound of the formula (II) with $R_3=H$ and $R_4=H$; theaflavin monogallate A, which is a compound of the formula (II) with $R_3=$3,4,5-trihydroxy benzoyl group and $R_4=H$; theaflavin monogallate B, which is a compound of the formula (II) with $R_3=H$ and $R_4=$3,4,5-trihydroxy benzoyl group; and theaflavin digallate, which is a compound of the formula (II) with $R_3=$3,4,5-trihydroxy benzoyl group and $R_4=$3,4,5-trihydroxy benzoyl group.

The above described tea polyphenol compounds can be prepared from tea leaves as the starting material and a method for the preparation thereof and a typical example of the product composition are described, for example, in Japanese Patent Kokai 59-219384, 60-13780 and 61-130285 and elsewhere.

When the inventive medicament against infection with mycoplasma is to be processed into a medicament form or used as an additive in food, the above described tea polyphenol as the effective ingredient or tea as such is admixed with the base without or with dilution with water or alcohol. A preferable concentration is in the range from 0.2% to 10% for tea or about 50 µg/ml for the tea polyphenol.

The above described preventive medicament against infection with mycoplasma comprises, as the effective ingredient, a natural product which is drinkable and can be taken in daily life in a considerably large volume so that it is absolutely free from the problem of undesirable side effects to the human body not only when it is used as a medicine, but also when it is used as an additive to food. Moreover, the effectiveness thereof is so high that infection with mycoplasma can be effectively inhibited by the addition thereof even in a very low concentration to provide a means for preventing infection with mycoplasma.

In the following, examples are given to illustrate the invention in more detail.

EXAMPLE 1

(1) Preparation of tea and catechins:

Test solutions of tea and catechin were prepared in the following manner. Thus, green tea, black tea or puh-ar tea was extracted for 3 hours at room temperature with a phosphate buffer solution having a pH of 7.0 in a dosage of 20 wt./vol. % followed by centrifugation at 15,000 rpm for 10 minutes to give a supernatant from which test solutions were prepared by dilution in concentrations of 20%, 4% and 0.4%. As the catechin compound, (−)epigallocatechin gallate which exhibited antibacterial and antitoxic activity, which is referred to as EGCg hereinbelow, was selected and dissolved in the same phosphate buffer solution in concentrations of 100 µg/ml, 20 µg/ml and 2 µg/ml to give the test solutions.

Similarly, theaflavin digallate, which is referred to as TF3 hereinbelow, was dissolved in the buffer solution to give a solution of 100 µg/ml concentration which was diluted 2-fold to give a solution of 50 µg/ml concentration which was used as the test solution.

(2) Preparation of microbial strains and the microbial suspension:

Four strains of mycoplasmas were used for the assay including *Mycoplasma pneumoniae* IID 815 and IID 817 originating in human, *M. salivarium* IID 878 isolated from human oral cavity and *M. orale* IID 880. Each of the *M. pneumoniae* strains was cultured aerobically for 5 to 6 days using the culture medium of Chanock et al. at 37° C. Each of the other strains was cultured by the GAS PAK method in the presence of carbon dioxide gas at 37° C. for 4 to 5 days. After completion of the culturing, the culture broth was centrifuged at 12,000 rpm for 50 minutes to collect the microbial cells. The cells washed with a phosphate buffer solution was redispersed in the phosphate buffer solution to give a suspension which was used in the assay.

(3) Assay of the mycoplasma-killing activity

Assay of the mycoplasma-killing activity was conducted in the following manner. Each of the diluted solutions of the teas, EGCg and TF3 was admixed with the same volume of the microbial suspension. The mycoplasma-added solution was diluted 10-fold to 10,000-fold and 10 µl portion of the solution, either immediately after dilution or after incubation for 3 hours at 37° C., was added dropwise to an agar culture medium of Chanock et al. The number of the colonies formed by culturing was counted under a microscope of 100 times magnification and the result was recorded as the colony-forming units CFU/ml as a measure for the evaluation of the mycoplasma-killing activity.

As is shown in the table below, green tea and black tea exhibited remarkable mycoplasma-killing activity against *M. pneumoniae* and *M. orale* so as to decrease the number of the microorganisms to 1/1000 or below even in a concentration of 0.2%. The puh-ar tea exhibited mycoplasma-killing activity within 3 hours in a concentration of 10% or 2%. On the other hand, the mycoplasma-killing activity against *M. salivarium* was obtained with the black tea in a concentration of 10% or 2% while no mycoplasma-killing activity was exhibited against this strain by the green tea and puh-ar tea irrespective of the concentration. The EGCg and TF3 exhibited remarkable mycoplasma-killing activity in a concentration of 50 µg/ml against each of these three species from the moment immediately after dilution.

TABLE 1

| Culture medium | Concentration (%) | M. orale As diluted | M. orale After 3 hours of incubation | M. salivarium As diluted | M. salivarium After 3 hours of incubation | M. pneumoniae As diluted | M. pneumoniae After 3 hours of incubation |
|---|---|---|---|---|---|---|---|
| Green tea | 10 | + | + | − | − | + | + |
|  | 2 | + | + | − | − | + | + |
|  | 0.2 | + | + | − | − | + | + |
| Black tea | 10 | + | + | + | ± | + | + |
|  | 2 | + | + | + | ± | + | + |
|  | 0.2 | + | + | − | − | + | + |
| Puh-ar tea | 10 | − | + | − | − | − | + |
|  | 2 | − | + | − | − | − | + |
|  | 0.2 | − | + | − | − | − | − |

+ (positive): decrease in the number of microorganisms by a factor of $10^2$ or larger as compared with the control
− (negative): decrease in the number of microorganisms by a factor of 10 or smaller

TABLE 2

| Culture medium | Concentration (µg/ml) | Factor of decrease in the number of microorganisms after addition of EGCg, CFU/ml As diluted | Factor of decrease in the number of microorganisms after addition of EGCg, CFU/ml After 3 hours of incubation* |
|---|---|---|---|
| EGCg added | 50 | $<<10^3$ | $<<10^3$ |
| EGCg added | 10 | $7.2 \times 10^4$ | $<<10^3$ |
| EGCg added | 1 | $2.8 \times 10^5$ | $1.4 \times 10^4$ |

TABLE 2-continued

| Culture medium | Concentration (μg/ml) | Factor of decrease in the number of microorganisms after addition of EGCg, CFU/ml | |
|---|---|---|---|
| | | As diluted | After 3 hours of incubation* |
| Control** | — | $4.1 \times 10^5$ | $3.5 \times 10^4$ |

*: culturing time at 37° C.
**: phosphate buffer solution alone added

TABLE 3

| Culture medium | Concentration (μg/ml) | Factor of decrease in the number of microorganisms after addition of EGCg, CFU/ml | |
|---|---|---|---|
| | | As diluted | After 3 hours of incubation* |
| EGCg added | 50 | $4.9 \times 10^4$ | $<<10^3$ |
| EGCg added | 10 | $5.7 \times 10^7$ | $8.5 \times 10^6$ |
| EGCg added | 1 | $5.7 \times 10^7$ | $2.4 \times 10^7$ |
| Control** | — | $3.6 \times 10^7$ | $3.5 \times 10^7$ |

*: culturing time at 37° C.
**: phosphate buffer solution alone added

TABLE 4

| Culture medium | Concentration (μg/ml) | Factor of decrease in the number of microorganisms after addition of EGCg, CFU/ml | |
|---|---|---|---|
| | | As diluted | After 3 hours of incubation* |
| EGCg added | 50 | $3.7 \times 10^4$ | $3.7 \times 10^4$ |
| EGCg added | 10 | $1.0 \times 10^8$ | $1.1 \times 10^7$ |
| EGCg added | 1 | $5.8 \times 10^7$ | $4.5 \times 10^7$ |
| Control** | — | $8.4 \times 10^7$ | $4.6 \times 10^7$ |

*: culturing time at 37° C.
**: phosphate buffer solution alone added

TABLE 5

| Culture medium | Concentration (μg/ml) | Factor of decrease in the number of microorganisms after addition, CFU/ml (as diluted) |
|---|---|---|
| TF3 added | 50 | $3.4 \times 10^4$ |
| EGCg added | 50 | $1.2 \times 10^4$ |
| Control** | — | $1.2 \times 10^7$ |

**: phosphate buffer solution alone added

What is claimed is:

1. A method of preventing infection in humans from mycoplasma comprising administering to said human, tea polyphenol extracted from tea in an amount sufficient to prevent infection from mycoplasma.

2. The method of claim 1 wherein the amount administered provides a concentration of said tea polyphenol of about 50 μg/ml.

3. The method of claim 1 wherein said tea polyphenol is selected from the group consisting of epigallocatechin gallate, epicatechin gallate, epigallocatechin, epicatechin, (+)catechin and the isomer thereof, free theaflavin, theaflavin monogallate A, theaflavin monogallate B and theaflavin digallate.

4. The method of claim 2 wherein said tea polyphenol is selected from the group consisting of epigallocatechin gallate, epicatechin gallate, epigallocatechin, epicatechin, (+)catechin and the isomer thereof, free theaflavin, theaflavin monogallate A, theaflavin monogallate B and theaflavin digallate.

5. The method of claim 9 wherein said tea polyphenol is epigallocatechin gallate.

6. The method of claim 9 wherein said tea polyphenol is epicatechin gallate.

7. The method of claim 9 wherein said tea polyphenol is epigallocatechin.

8. The method of claim 9 wherein said tea polyphenol is epicatechin.

9. The method of claim 9 wherein said tea polyphenol is (+)catechin and the isomer thereof.

10. The method of claim 9 wherein said tea polyphenol is free theaflavin.

11. The method of claim 9 wherein said tea polyphenol is theaflavin monogallate A.

12. The method of claim 9 wherein said tea polyphenol is theaflavin monogallate B.

13. The method of claim 9 wherein said tea polyphenol is theaflavin digallate.

14. The method of claim 3, wherein the mycoplasma is selected from the group consisting of Mycoplasma pneumoniae IID 815, *Mycoplasma pneumoniae* IID 817, *M. salivarium* IID 878 and *M. orale* IID 880.

15. The method of claim 3, wherein the tea polyphenol is orally administered.

* * * * *

UNITED STATES PATENT AND TRADEMARK OFFICE
CERTIFICATE OF CORRECTION

PATENT NO. : 5,104,901

DATED : April 14, 1992

INVENTOR(S) : SHIMAMURA et al

It is certified that error appears in the above-identified patent and that said Letters Patent is hereby corrected as shown below:

Title Page, right column, above the first line which starts "4,004,038", insert

--4,840,966    6/1989    Hara et al
4,613,672    9/1986    Hara
4,673,530    6/1987    Hara--.

Column 6, line 29 (claim 5), delete "claim 9", and insert --claim 3--.

Column 6, line 31 (claim 6), delete "claim 9", and insert --claim 3--.

Column 6, line 33 (claim 7), delete "claim 9", and insert --claim 3--.

Column 6, line 35 (claim 8), delete "claim 9", and insert --claim 3--.

Column 6, line 37 (claim 9), delete "claim 9", and insert --claim 3--.

Column 6, line 39 (claim 10), delete "claim 9", and insert --claim 3--.

UNITED STATES PATENT AND TRADEMARK OFFICE
CERTIFICATE OF CORRECTION

PATENT NO.   : 5,104,901
DATED        : April 14, 1992
INVENTOR(S)  : SHIMAMURA et al It is certified that error appears in the above-identified patent and that said Letters Patent is hereby corrected as shown below:

Column 6, line 41 (claim 11), delete "claim 9", and insert --claim 3--.

Column 6, line 43 (claim 12), delete "claim 9", and insert --claim 3--.

Column 6, line 45 (claim 13), delete "claim 9", and insert --claim 3--.

Signed and Sealed this

Fourth Day of October, 1994

Attest:

BRUCE LEHMAN

*Attesting Officer*   *Commissioner of Patents and Trademarks*